United States Patent
Schwind et al.

(10) Patent No.: US 7,615,523 B2
(45) Date of Patent: Nov. 10, 2009

(54) LENS CARE PRODUCT CONTAINING DEXPANTHENOL

(75) Inventors: Peter Schwind, Hösbach-Rottenberg (DE); Anton Scherer, Frammersbach (DE)

(73) Assignee: Novartis AG, Basel (CH)

( * ) Notice: Subject to any disclaimer, the term of this patent is extended or adjusted under 35 U.S.C. 154(b) by 247 days.

(21) Appl. No.: 11/544,401

(22) Filed: Oct. 6, 2006

(65) Prior Publication Data

US 2007/0027048 A1 Feb. 1, 2007

(51) Int. Cl.
*C11D 3/00* (2006.01)

(52) U.S. Cl. .................. 510/112; 422/28; 514/840

(58) Field of Classification Search ............... 510/112; 422/28; 514/840
See application file for complete search history.

(56) References Cited

U.S. PATENT DOCUMENTS

| | | | |
|---|---|---|---|
| 4,525,346 A | 6/1985 | Stark | 424/80 |
| 5,290,813 A * | 3/1994 | Clark et al. | 514/563 |
| 5,300,296 A | 4/1994 | Holly et al. | 424/427 |
| 5,422,073 A | 6/1995 | Mowrey-McKee | 422/28 |
| 5,460,808 A | 10/1995 | Mausner | 424/70.7 |
| 5,500,186 A | 3/1996 | Mowrey-McKee | 422/28 |
| 5,593,637 A | 1/1997 | Mowrey-McKee | 422/28 |
| 5,756,045 A | 5/1998 | Mowrey-McKee et al. | 422/28 |
| 5,817,277 A | 10/1998 | Mowrey-McKee | 422/28 |
| 6,106,828 A | 8/2000 | Bisgard-Frantzen et al. | 424/94.1 |
| 6,172,017 B1 | 1/2001 | Groemminger et al. | 510/112 |
| 6,440,911 B1 * | 8/2002 | Bettiol et al. | 510/137 |
| 2003/0190347 A1 * | 10/2003 | Supersaxo et al. | 424/450 |
| 2004/0057980 A1 | 3/2004 | Wagenaar | 425/42 |
| 2006/0148665 A1 * | 7/2006 | Smith | 510/126 |

FOREIGN PATENT DOCUMENTS

| | | |
|---|---|---|
| EP | 0 610 655 B1 | 1/1994 |
| JP | 2002265357 A * | 9/2002 |
| JP | 2003089601 A * | 3/2003 |
| WO | WO 94/09794 | 5/1994 |
| WO | WO 99/06071 | 2/1999 |
| WO | WO 99/26669 | 6/1999 |
| WO | WO 99/27060 | 6/1999 |

OTHER PUBLICATIONS

European Search Report (extended).
Document D3 (front page, copy right page, and pp. 649 and 807 of "The Condensed Chemical Dictionary", Ninth Edition, 1977, van Nostrand Reinhold Company.
International Search Report Apr. 2, 2002.
Rompp Chemie Lexicon 10, Georg Thieme Verlag Stuttgart, New York s. 3107-3109.
International Search Report.
PCT Written Opinion.
WO-A-9906071, Jan. 17, 2003, IPEA.
D3:Rompp Chemie EPA EPO OEB.
Gobbels, Martin Grob, Dorothea, "Klinische Studie zur Wirksamkeit eines dexpanthenolhaltigen Tranenersatzmittels siccaprotect bei der behandlung Trockner Augen," Klin Monatsbl Augenheikunde, 1996; 209, pp. 84-88 (abstract translated in English).
Norwegian Official Action regarding Patent Application No. 20033161 dated Apr. 7, 2009.

* cited by examiner

*Primary Examiner*—Gregory E Webb
(74) *Attorney, Agent, or Firm*—Sheng Hsin-Hu

(57) ABSTRACT

The present invention relates to contact lens care product comprising dexpanthenol. The invention similarly relates to the usage of a contact lens care compositions of this kind for cleaning and optionally disinfecting contact lenses.

12 Claims, No Drawings

LENS CARE PRODUCT CONTAINING DEXPANTHENOL

The present invention relates to a contact lens care product for hard and soft contact lenses, containing dexpanthenol or preferably dexpanthenol in combination with sorbitol.

Dexpanthenol, an alcohol of pantothenic acid, also called Provitamin B5, D-pantothenyl alcohol or D-panthenol, has been used for a long time for healing wounds or in the field of medicinal skin care. It has now surprisingly been found that dexpanthenol can also be used very effectively as a constituent in contact lens care products. The compound has good cleansing action and, in addition, stabilises the lachrymal film when inserting the contact lenses. Vortex motion of the lachrymal liquid can occur through the insertion of contact lenses, namely because of mechanical eruption or through surface-active substances optionally present in the contact lens solution and can lead to severe loss of the aqueous lachrymal layer. It was found that dexpanthenol stabilises the lachrymal film and prevents severe losses of the aqueous layer. This guards against the appearance of dryness, which can lead to a reduced lachrymal film.

The subject of the present invention is therefore a contact lens care composition containing dexpanthenol. The invention similarly relates to the use of dexpanthenol for cleaning and disinfecting contact lenses.

Dexpanthenol is preferably used in the contact lens care compositions according to the invention in an amount of ca. 0.2 to 10 percent by weight, especially in an amount of ca. 0.5 to 5 percent by weight, more preferably in an amount of ca. 0.5 to 4 percent by weight, most preferably in an amount of 1 to 3 percent by weight, based on the total amount of contact lens care compositions which is advantageously formulated in aqueous solution.

Apart from dexpanthenol and water, the contact lens care compositions according to the invention generally contain one or more other constituents, e.g. buffer substances, substances that affect the tonicity, surface-active substances, substances that affect viscosity, complexing agents and/or antimicrobial compounds. Although it is generally unnecessary, an enzymatic cleaning substance may also be present in the contact lens care products according to the invention. The amounts of these or other conventional additives used in the contact lens care compositions according to the invention are variable within the limits known to the person skilled in the art.

The contact lens care products according to the invention are preferably formulated in such a way that they are isotonic with the lachrymal fluid.

A solution which is isotonic with the lachrymal fluid is generally understood to be a solution whose concentration corresponds to the concentration of a 0.9% sodium chloride solution. Deviations from this concentration are possible throughout, provided that the contact lenses to be treated are not damaged. The isotonicity with the lachrymal fluid, or even another desired tonicity, may be adjusted by adding organic or inorganic substances which affect the tonicity. The former may be used e.g. in amounts of about 1 to 4.5 percent by weight, and the latter in amounts of about 0.1 to 1.3 percent by weight. In general the amount to be added of the substance which affects tonicity, is such that the tonicity of the composition according to the invention is in particular in the range 200 to 450 milliosmol, preferably in the range 270 to 330 milliosmol. Typical organic substances of this kind are, for example, glycerol, urea, propylene glycol or sugar such as mannitol or sorbitol, and typical inorganic substances of this kind are in particular potassium chloride or sodium chloride. Mixtures of these compounds with one another may also be used according to the invention.

Suitable surface-active substances are named for example in EP-A2-180 309. Especially suitable representatives that may be used according to the invention are, for example, the poloxamer types (polyethylene glycol-polypropylene glycol block copolymers, e.g. Pluronic® or Pluronic® R types) or miranol types. Other representatives are known to the person skilled in the art. These substances may be used, for example, in amounts of up to 20 percent by weight, especially in amounts of 0.4 to 5 percent by weight, based on the total amount of contact lens care composition.

Suitable substances which affect viscosity are likewise known to the person skilled in the art. Especially suitable representatives which may be used according to the invention are those named here, for example polyvinyl alcohol, methyl cellulose, hydroxyethyl cellulose, hydroxypropylmethyl cellulose or polyacrylic acid. Typical amounts of these substances are 0.1 to 2 percent by weight, based on the total amount of contact lens care composition.

One especially suitable complex former is in particular ethylenediamine tetraacetic acid, abbreviated to EDTA, or salts thereof such as sodium salts. Typical amounts of these substances are 0.01 to 1 percent by weight, based on the total amount of contact lens care composition.

One group of suitable antimicrobial agents is represented by quaternary ammonium salts. Another example of preferred antimicrobial agents is biguanides, e.g. hexamethylene biguanides or water-soluble polymers, e.g. a polyaminopropyl biguanide, or a suitable salt thereof. One preferred antimicrobial agent is PHMB (polyhexamethylene biguanide).

The antimicrobial agent is preferably used in the contact lens care composition according to the invention in an amount of 0.1 to 100 ppm (0.00001-0.01 percent by weight), especially in an amount of 0.5 to 50 ppm (0.00005-0.005 percent by weight), and most particularly in an amount of 1 to 10 ppm (0.0001-0.001 percent by weight), e.g. 1.2 or 5 ppm, based on the total amount of contact lens care composition.

In the context of the present invention, a suitable salt is generally understood to be a water-soluble salt which is advantageously ophthalmologically acceptable. Suitable salts are those with inorganic or organic acids, for example hydrochlorides, hydrobromides, borates, acetates, gluconates, sulfonates, maleates, ascorbates, tartrates or citrates.

Suitable buffer substances as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (trometamol, 2-amino-2-hydroxymethyl-1,3-propanediol), phosphate buffers, e.g. $Na_2HPO_4$, $NaH_2PO_4$, and $KH_2PO_4$ or mixtures thereof.

The pH value of the care compositions is preferably from e.g. 5 to 8, preferably from 6 to 8, most preferably from 7 to 7.6.

One preferred embodiment of the present invention relates to a contact lens care compositions containing dexpanthenol and D-sorbit.

D-sorbit, a hexavalent sugar alcohol, also called sorbitol, D-sorbitol or D-glucitol, is used in gels as a moisture-retaining agent and plasticiser.

The addition of D-sorbit to adjust the tonicity of contact lens care products is known. GB 2,205,175 and U.S. Pat. No. 3,888,782 describe sorbit as a carrier material for the preparation of powder mixtures for contact lens care products. It has now surprisingly been found that the combination dexpanthenol and D-sorbit can be used effectively as a constituent in contact lens care compositions. The combination dexpanthenol and D-sorbit possesses a favourable cleansing action and also stabilises the lachrymal film after inserting the contact lenses, whereupon a heavy loss of the aqueous layer is prevented. This guards against the appearance of dryness, which can lead to a reduced lachrymal film. The usage of the active ingredient combination dexpanthenol and D-sorbit also substantially improves comfort when wearing contact lenses. Negative effects caused by surface-active substances and preservatives are reduced and the contact lenses are prevented from drying out.

Furthermore, it has been shown in studies that the addition of dexpanthenol and D-sorbit is not cytotoxic and does not have negative effects on the antimicrobial efficacy of the solutions. It has surprisingly been found that the addition of sorbit substantially increases the microbiological efficacy of antimicrobial compounds present in the contact lens care compositions according to the invention, e.g. of PHMB, without resulting in negative effects as regards toxicity.

Dexpanthenol is preferably used in the preferred sorbit-containing contact lens care compositions according to the invention in the amount indicated above, whereby the said preferences apply.

D-sorbit is used in the preferred contact lens care compositions according to the invention in an amount of about 0.4 to about 18 percent by weight, especially in an amount of 0.6 to 8 percent by weight, more preferably in an amount of 0.8 to 6 percent by weight, most preferably in an amount of 1 to 3 percent by weight, based on the total amount of contact lens care composition which is advantageously formulated in aqueous solution.

The preferred contact lens care compositions according to the invention advantageously contain, in addition to dexpanthenol, D-sorbit and water, one or more other constituents, e.g. buffer substances, further substances that affect the tonicity, surface-active substances, substances that affect viscosity, complexing agents and/or antimicrobial compounds, whereby the meanings and preferences given above apply. Although it is generally unnecessary, an enzymatic cleaning substance may also be present in the preferred contact lens care compositions according to the invention. The amounts in which these or other conventional additives are contained in the contact lens care compositions according to the invention, which contain dexpanthenol and D-sorbit, correspond to the amounts mentioned above, including the preferences given therein.

The contact lens care compositions according to the invention are suitable for all kinds of contact lenses. This includes in particular the so-called hard and soft contact lenses, and also the so-called hard-flexible or highly gas-permeable contact lenses. The contact lens care compositions according to the invention have cleaning action and, in addition, optionally have antimicrobial action. Depending on the intended purpose of use, the contact lens care compositions according to the invention may be used as cleaning agents, as disinfectants, or e.g. as a solution in which to store, rinse, moisten or soak the contact lenses. Preferably, dexpanthenol or the combination of dexpanthenol and D-sorbit are respectively used in so-called all-in-one solutions, but may also be advantageously added to other contact lens care products, for example neutralisation solutions, hard lens care compositions, storing and disinfecting solutions. All these solutions are notable for their good tolerance.

The contact lens care compositions according to the invention are produced in known manner, in particular by means of conventional mixing of the constituents with water or dissolving the constituents in water.

The compositions according to the invention are especially suitable for cleaning and, where appropriate, for disinfecting contact lenses. The contact lens care compositions according to the invention are used in known manner, e.g. by bringing the contact lens into contact with the contact lens care composition for a period of time that is sufficient to clean or disinfect it. Depending on the lens type and the degree of soiling, a sufficient time span ranges from a few minutes to about 24 hours, preferably up to about 4 to 12 hours; a treatment time of e.g. 1 to 12 hours, preferably 2 to 8 hours and in particular 4 to 6 hours, has proved to be especially practicable.

One preferred solution according to the invention contains, for example, dexpanthenol, one or more buffer substances, PHMB, sodium chloride or potassium chloride and a complexing agent, preferably EDTA.

An especially preferred solution according to the invention thus contains e.g.:

| | |
|---|---|
| dexpanthenol | 5 to 20 g/l |
| NaCl or KCl | 3 to 9 g/l |
| PHMB | 0.0005 to 0.05 g/l |
| EDTA | 0.1 to 2 g/l | as well as buffer substances which stabilise a pH value of 6 to 8, e.g. $Na_2HPO_4$, $NaH_2PO_4$, TRIS, and water.

A further preferred solution according to the invention contains, for example, dexpanthenol, D-sorbit, one or more buffer substances, PHMB, sodium chloride or potassium chloride and a complexing agent, preferably EDTA.

An especially preferred solution according to the invention thus contains e.g.:

| | |
|---|---|
| dexpanthenol | 5 to 20 g/l |
| D-sorbit | 10 to 30 g/l |
| NaCl or KCl | 0 to 5 g/l, e.g. 0 g/l or 1 to 5 g/l |
| PHMB | 0.0005 to 0.05 g/l |
| EDTA | 0.1 to 2 g/l | as well as buffer substances which stabilise a pH value of 6 to 8, e.g. $Na_2HPO_4$, $NaH_2PO_4$, TRIS, and water.

The above-mentioned preferred solutions may also contain:

| | |
|---|---|
| a surface-active substance | 0.1 to 2 g/l |
| a compound which affects the viscosity | 0.1 to 2 g/l |

The following examples serve to illustrate the invention. They are in no way intended to limit the subject matter of the invention, especially the subject matter of the examples.

EXAMPLE 1

Formulation for a Contact Lens Care Composition

A contact lens care composition is produced by mixing together the following components:

| | |
|---|---|
| dexpanthenol | 10.0 g/l |
| EDTA | 1.0 g/l |
| sodium chloride | 7.0 g/l |
| TRIS buffer | 2.5 g/l |
| Methocel E5 (cellulose ether product) | 0.5 g/l |

-continued

| | |
|---|---|
| PHMB | 0.001 g/l |
| aqua purificata | ad 1000 ml. |

EXAMPLE 2

Formulation for a Contact Lens Care Composition

A contact lens care composition is produced by mixing together the following components:

| | |
|---|---|
| dexpanthenol | 10.0 g/l |
| EDTA | 1.0 g/l |
| sodium chloride | 7.0 g/l |
| TRIS buffer | 2.5 g/l |
| PHMB | 0.001 g/l |
| aqua purificata | ad 1000 ml |

EXAMPLE 3

Formulation for a Contact Lens Care Composition

A contact lens care composition is produced by mixing together the following components:

| | |
|---|---|
| dexpanthenol | 10.0 g/l |
| EDTA | 0.25 g/l |
| sodium chloride | 8.6 g/l |
| disodium hydrogen phosphate | 0.072 g/l |
| sodium dihydrogen phosphate | 0.622 g/l |
| PHMB | 0.001 g/l |
| Poloxamer 407 | 1.0 g/l |
| aqua purificata | ad 1000 ml |

EXAMPLE 4

Formulation for a Contact Lens Care Composition

A contact lens care composition is produced by mixing together the following components:

| | |
|---|---|
| dexpanthenol | 10.0 g/l |
| D-sorbit | 18.0 g/l |
| EDTA | 1.0 g/l |
| TRIS buffer | 2.5 g/l |
| Methocel E5 | 0.5 g/l |
| PHMB | 0.001 g/l |
| aqua purificata | ad 1000 ml. |

EXAMPLE 5

Formulation for a Contact Lens Care Composition

A contact lens care composition is produced by mixing together the following components:

| | |
|---|---|
| dexpanthenol | 10.0 g/l |
| D-sorbit | 18 g/l |
| EDTA | 1.0 g/l |
| TRIS buffer | 2.5 g/l |
| PHMB | 0.001 g/l |
| aqua purificata | ad 1000 ml |

EXAMPLE 6

Formulation for a Contact Lens Care Composition

A contact lens care composition is produced by mixing together the following components:

| | |
|---|---|
| dexpanthenol | 10.0 g/l |
| D-sorbit | 18 g/l |
| EDTA | 0.25 g/l |
| disodium hydrogen phosphate | 0.072 g/l |
| sodium dihydrogen phosphate | 0.622 g/l |
| PHMB | 0.001 g/l |
| Poloxamer 407 | 1.0 g/l |
| aqua purificata | ad 1000 ml |

EXAMPLE 7

Formulation for a Contact Lens Care Composition

A contact lens care composition is produced by mixing together the following components:

| | |
|---|---|
| dexpanthenol | 20.0 g/l |
| D-sorbit | 18.8 g/l |
| EDTA | 0.25 g/l |
| sodium dihydrogen phosphate | 4.6 g/l |
| TRIS | 3.3 g/l |
| PHMB | 0.001 g/l |
| Pluronic F127 | 1.0 g/l |
| aqua purificata | ad 1000 ml |

EXAMPLE 8

Formulation for a Hard Lens Care Composition

A contact lens care composition is produced by mixing together the following components:

| | |
|---|---|
| dexpanthenol | 20.0 g/l. |
| D-sorbit | 18.8 g/l |
| sodium borate | 0.05 g/l |
| boric acid | 5.0 g/l |
| hydroxyethyl cellulose | 3.4 g/l |
| Pluronic 17R4 | 1.0 g/l |
| sodium perborate | 0.28 g/l |
| stabiliser (Dequest 2060 S) | 0.12 g/l |
| aqua purificata | ad 1000 ml |

What we claim is:

1. Contact lens care composition comprising dexpanthenol, D-sorbit and 2-amino-2-hydroxymethyl-1,3-propanediol.

2. Contact lens care composition according to claim 1, comprising an aqueous solution comprising 0.5 to 4 percent by weight, preferably 1 to 3 percent by weight, of dexpanthenol, based on the total weight of the contact lens care composition.

3. Contact lens care composition according to claim 2, comprising 0.8 to 6 percent by weight, preferably 1 to 3 percent by weight, of D-sorbit, based on the total weight of the contact lens care composition.

4. Contact lens care composition according to claim 1, which comprises one or more further constituents selected from the group consisting of buffer substances, substances that affect the tonicity, surface-active substances, substances that affect viscosity, complexing agents and/or antimicrobial compounds.

5. Contact lens care composition according to claim 1, which comprises dexpanthenol, one or more buffer substances, PHMB, sodium chloride or potassium chloride and a complexing agent.

6. Contact lens care composition according to claim 5, which contains

| | |
|---|---|
| dexpanthenol | 5 to 20 g/l |
| NaCl or KCl | 3 to 9 g/l |
| PHMB | 0.0005 to 0.05 g/l |
| EDTA | 0.1 to 2 g/l | as well as buffer substances and water, and it has a pH value of 6 to 8.

7. Contact lens care composition according to claim 3, which comprises dexpanthenol, D-sorbit, one or more buffer substances, PHMB, sodium chloride or potassium chloride and a complexing agent.

8. Contact lens care composition according to claim 7, which comprises

| | |
|---|---|
| dexpanthenol | 5 to 20 g/l |
| D-sorbit | 10 to 30 g/l |
| NaCl or KCl | 0 to 5 g/l |
| PHMB | 0.0005 to 0.05 g/l |
| EDTA | 0.1 to 2 g/l | as well as buffer substances and water, and it has a pH value of 6 to 8.

9. Contact lens care composition according to claim 6, which comprises, in addition, a surface-active substance.

10. Use of a contact lens care composition according to claim 1, for cleaning and optionally disinfecting a contact lens.

11. Method for cleaning and optionally disinfecting a contact lens, wherein a contact lens care composition according to claim 1 is brought into contact with a contact lens for a period of time that is sufficient to clean and optionally disinfect it.

12. Method for cleaning and optionally disinfecting a contact lens, wherein a contact lens care composition according to claim 3 is brought into contact with a contact lens for a period of time that is sufficient to clean and optionally disinfect it.

* * * * *